United States Patent [19]

Gschwend et al.

[11] 4,124,593
[45] Nov. 7, 1978

[54] AROMATIC DICARBOXIMIDES

[75] Inventors: Heinz W. Gschwend, New Providence, N.J.; Malvin J. Hillman, Liverpool, N.Y.

[73] Assignee: Ciba-Geigy Corporation, Ardsley, N.Y.

[21] Appl. No.: 697,494

[22] Filed: Jun. 18, 1976

Related U.S. Application Data

[63] Continuation-in-part of Ser. No. 631,789, Nov. 13, 1975, Pat. No. 4,025,505, which is a continuation-in-part of Ser. No. 547,063, Feb. 4, 1975, abandoned, which is a continuation-in-part of Ser. No. 449,872, Mar. 11, 1974, Pat. No. 3,941,883.

[51] Int. Cl.$^2$ ............................................. C07D 209/34
[52] U.S. Cl. ............................ 260/326 N; 260/346.7; 260/578; 424/274; 562/480; 562/409
[58] Field of Search ...................................... 260/326 N

[56] References Cited

U.S. PATENT DOCUMENTS

| | | | |
|---|---|---|---|
| 2,911,410 | 11/1959 | Ramsay | 260/326 N |
| 3,533,785 | 10/1970 | Fox et al. | 260/326 N X |
| 3,941,883 | 3/1976 | Gschwend et al. | 424/274 |

FOREIGN PATENT DOCUMENTS

| | | | |
|---|---|---|---|
| 901,420 | 7/1962 | United Kingdom | 260/326 N |
| 1,241,470 | 8/1971 | United Kingdom | 260/326 N |
| 901,420 | 7/1962 | United Kingdom | 260/326 N |

*Primary Examiner*—Ethel G. Love
*Attorney, Agent, or Firm*—Theodore O. Groeger

[57] ABSTRACT

N-(4-aminophenyl)-aromatic dicarboximides, e.g. those of the formula

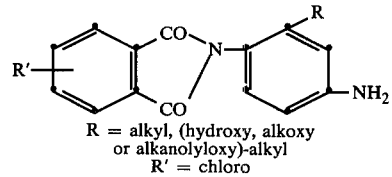

R = alkyl, (hydroxy, alkoxy or alkanolyloxy)-alkyl
R' = chloro or salts thereof are anticonvulsants.

5 Claims, No Drawings

AROMATIC DICARBOXIMIDES

CROSS REFERENCES TO RELATED APPLICATIONS

This is a continuation-in-part of application Ser. No. 631,789, filed Nov. 13, 1975, now U.S. Pat. No. 4,025,505, which in turn is a continuation-in-part of application Ser. No. 547,063, filed Feb. 4, 1975, now abandoned which in turn is a continuation-in-part of application Ser. No. 449,872, filed Mar. 11, 1974, now U.S. Pat. No. 3,941,883.

BACKGROUND OF THE INVENTION

Compounds of the above formula, wherein at least one of R and R' is hydrogen, are disclosed in U.S. Pat. No. 3,767,805 or British Pat. No. 901,420 as intermediates in the preparation of "α-(cyclic tert. aminophenyl)-aliphatic acids" or "azo coloring matters" respectively. Surprisingly it was found that by properly selecting substitutents and their relative positions within the aromatic nuclei of said dicarboximides, highly potent anticonvulsant agents are obtained.

SUMMARY OF THE INVENTION

The present invention concerns and has for its object the provision of novel N-(4-aminophenyl)-aromatic dicarboximides, more particularly of those corresponding to Formula I

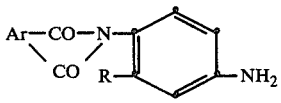
(I)

wherein Ar is chloro-1,2-phenylene and R is lower alkyl, (hydroxy, lower alkoxy or lower alkanoyloxy)-lower alkyl, or pharmaceutically acceptable salts thereof, and of corresponding pharmaceutical compositions and of methods for the preparation and application of these products, which are useful anticonvulsant agents, for example in the treatment or management of epilepsy or other spastic conditions.

DESCRIPTION OF THE PREFERRED EMBODIMENTS

The chloro-1,2-phenylene radical Ar contains the chlorine atom preferably in the 4-position and the lower alkyl group R is preferably methyl or ethyl. The substituted lower alkyl group R is preferably α-(hydroxy, methoxy, ethoxy or acetoxy)-(methyl or ethyl). The term "lower", referred to above and hereinafter in connection with organic radicals or compounds respectively, defines such with up to 4, especially up to 2 carbon atoms.

The above-mentioned salts of the amines of Formula I are preferably those of the therapeutically useful acids listed below, especially those with a pK of at most 2.4.

The compounds of the invention exhibit valuable pharmacological properties, primarily anticonvulsant activity, as can be demonstrated in animal tests, using advantageously mammals, such as mice or rats, as test objects. Said compounds can be applied to the host suffering from agitation and/or convulsions either enterally or parenterally, e.g. orally or intraperitoneally, for example in the form of aqueous solutions or starchy suspensions. The oral or intraperitoneal dosage may range between about 1 and about 800 mg/kg/day, preferably between about 5 and 500 mg/kg/day or especially between about 10 and about 50 mg/kg/day. Anticonvulsant effects are observed, for example, by the protection of said mammals against electrically or chemically induced seizures, such as mouse or rat minimum or maximum electroshock, or seizures caused by 1,5-pentamethylenetetrazole, picrotoxin, thiosemicarbazide or strychnine. According to the former test the compounds of the invention, for example, the N-(4-amino-o-tolyl)-4-chlorophthalimide, an illustrative member thereof, are administered to the animals either orally or intraperitoneally and one or two hours later, preferably at peak effect, they are given an electric shock, e.g. to mize 50 milliamperes of current and 0.2 second duration through corneal electrodes, from which all animals recover. Those animals not exhibiting a tonic (hind limb) extensor seizure are considered protected.

They are also given the compounds of the invention, either orally or intraperitoneally, and one hour later, for example, 24 mg/kg 1,5-pentamethylenetetrazole intravenously to rats. They are checked immediately for the presence of clonic seizures and all animals not exhibiting them are also considered protected. Furthermore, the overt effects of the compounds of Formula I are observed in rats 1/2, 1,2 and 20 hours after various oral or intraperitoneal doses and $ED_{50}$ values are estimated for various effects, e.g. muscle tone or ataxia, indicating skeletal muscle relaxing activity. According to the test results observed, the compounds of the invention are useful anticonvulsant agents, for example in the treatment or management of epilepsy or other spastic conditions. They are also useful intermediates in the preparation of other valuable products, preferably of pharmacologically active compounds, e.g. related anti-inflammatory agents.

Preferred compounds of the invention are those of Formula I, wherein Ar is 4-chloro-1,2-phenylene and R is alkyl, α-(hydroxy, alkoxy or alkanoyloxy-alkyl with up to 4 carbon atoms, or a therapeutically acceptable acid addition salt thereof.

More preferred on account of said effects are those compounds of Formula I, wherein Ar is 4-chloro-1,2-phenylene and R is methyl, ethyl, or α-(hydroxy, methoxy, ethoxy or acetoxy)-(methyl or ethyl), or a therapeutically acceptable acid addition salt thereof.

Outstanding activity is exhibited by the N-(4-amino-o-tolyl)-4-chlorophthalimide, or a therapeutically acceptable acid addition salt thereof, preferably the methane sulfonate thereof.

The compounds of the invention are prepared according to methods known per se. For example, they are obtained by reducing a compound of Formula III

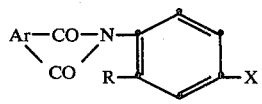
(III)

wherein X is a nitro, azido or azo group and, if desired, converting any resulting compound into another compound of the invention.

An azo group X is preferably derived from an isocyclic aromatic radical, e.g. phenyl, or H—Ar. Preferred radicals X are: $NO_2$, $N_3$ and $C_6H_5$—$N_2$. They are converted into amino by conventional reduction, for example, with the use of catalytically activated or nascent hydrogen, e.g. hydrogen in the presence of platinum, palladium or nickel catalysts, e.g. Raney nickel, or generated by the action of non-precious metals, e.g. zinc or iron, on acids, such as mineral acids, e.g. hydrochloric or sulfuric acid, or with the use of reducing agents, preferably salts of elements of the 4th to 6th group of the Periodic Table and being in a low oxidation state, such as titanous, stannous or chromous halides, ammonium polysulfides or alkali metal hydrosulfites.

Another process for the preparation of the compounds of this invention consists in hydrolyzing a compound of Formula III, wherein X is an isocyanato or acylamino group and, if desired, converting any resulting compound into another compound of the invention. An acylamino group is preferably derived from a lower alkanoic or aralkanoic acid or carbonic acid half-ester containing as aromatic radical either phenyl or H—Ar. Preferred radicals X are NCO, $C_mH_{2m+1}$—CONH, $C_mH_{2m+1}$—OCONH, $C_6H_5$—CONH or $C_6H_5CH_2OCONH$, wherein m is 1 to 7. These acylated amino groups are converted into amino by acidic or basic hydrolysis, the isocyanato group (for example formed in the course of the Schmidt-reaction) preferably with strong inorganic acids, such as hydrochloric, sulfuric or phosphoric acid, and the other acylamino groups preferably with the use of aqueous bases, such as aqueous alkali metal hydroxides or carbonates, or quaternary ammonium hydroxides, e.g. sodium hydroxide, potassium carbonate or trimethylbenzyl-ammonium hydroxide. Care should be taken in said hydrolysis, in order to prevent the hydrolytic opening of the imide moiety.

The compounds of the invention so obtained can be converted into a corresponding acid addition salt, for example by reacting it with an inorganic or organic acid, such as a therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, aminosalicylic, pamoic, nicotinic, mthanesulfonic, ethanesulfonic, hydroxy-ethanesulfonic, ethylenesulfonic, benzenesulfonic, halogenbenzenesulfonic, toluenesulfonic, naphthalenesulfonic, sulfanilic, or cyclohexylsulfamic acid, preferably those with a pK of at most 2.4.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example by separation of diastereomeric salts thereof, e.g. by the fractional crystallization of d- or l-tartrates.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. As mentioned above, isocyanates are formed from the corresponding acid azides and acylamino compounds may be formed in the formation of the cyclic starting materials from their acyclic precursors. In the process of the invention, those starting materials are advantageously selected, which yield the above-described preferred embodiments of the invention.

The starting material used is known or, if new, can be prepared according to the methods described for known analogs thereof, or by the methods illustrated in the examples herein.

The pharmacologically active compounds of the invention are useful in the manufacture of pharmaceutical compositions containing an effective amount thereof in conjunction or admixture with excipients suitable for either enteral, e.g. oral, or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees Centigrade, all parts wherever given are parts by weight, and all evaporations are carried out under reduced pressure.

EXAMPLE 1

The mixture of 1.65 g of N-(4-nitro-o-tolyl)-3-chlorophthalimide, 200 ml of ethyl acetate and 0.92 g of pre-washed Raney nickel is hydrogenated at 3.1 atm. and room temperature until the hydrogen uptake ceases. It is filtered, evaporated and the residue recrystallized from methanol, to yield the N-(4-amino-o-tolyl)-3-chlorophthalimide of the formula

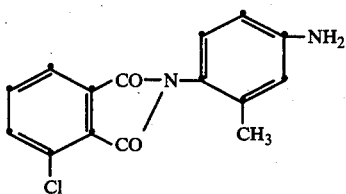

melting at 209°–211°.

The starting material is prepared as follows: The mixture of 3.0 g of 3-chlorophthalic anhydride, 2.5 g of 4-nitro-o-toluidine and 200 ml of xylene is refluxed for 2 days on a water-trap and evaporated. The residue is taken up in chloroform, the mixture filtered, the filtrate chromatographed on silica gel and the column eluted with chloroform-ethyl acetate (9:1), to yield the N-(4-nitro-o-tolyl)-3-chlorophthalimide melting at 229.232°.

EXAMPLE 2

The mixture of 12.4 g of N-(4-nitro-o-tolyl)-4-chlorophthalimide, 1.0 lt. ethyl acetate and 10 ml of an ethanolic suspension containing 6.9 g of Raney nickel is hydrogenated at 2.8 atm. and room temperature for 12 hours. It is filtered, concentrated to about half of its original volume and the precipitate formed collected, to yield the N-(4-amino-o-tolyl)-4-chlorophthalimide melting at 201°–203°.

The starting material is prepared as follows: The mixture of 36 g of 4-chlorophthalic acid and 250 ml of acetic anhydride is refluxed for 2 hours and evaporated. The residual 4-chlorophthalic anhydride is dried in a high vacuum and 27.8 g thereof refluxed in 480 ml of toluene together with 23.1 g of 4-nitro-o-toluidien for 1 day. It is cooled, the precipitate filtered off, washed with benzene and dried at 80°/0.1 mmHg, to yield the corresponding amide melting at 185°–188°.

The mixture of 35 g thereof and 250 ml of acetic anhydride is refluxed for 2 hours and evaporated. The residue is dried, taken up in the minimum amount of hot ethyl acetate, the solution treated with charcoal, filtered, the filtrate cooled and the precipitate formed collected, to yield N-(4-nitro-o-tolyl)-4-chlorophthalimide melting at 221°–222°.

EXAMPLE 3

The mixture of 3.0 g of N-(4-nitro-2-hydroxymethylphenyl)-4-chlorophthalimide, 1.5 g of Raney nickel and 250 ml of ethyl acetate is hydrogenated at room temperature and atmospheric pressure until the hydrogen uptake ceases. It is filtered, the filtrate evaporated and the residue recrystallized from ethyl acetate-diethyl ether, to yield the N-(4-amino-2-hydroxymethylphenyl)-4-chlorophthalimide melting at 228°–230°.

The starting material is prepared as follows: The solution of 23.4 g of t-butylhypochlorite in 20 ml of methylene chloride is added to that of 30.0 g of 4-nitroaniline and 27.0 g of dimethyl thioether in 650 ml of acetonitrile and 200 ml of methylene chloride while stirring at −40° under nitrogen. After 4 hours the temperature is raised to −20° and maintained there for three hours. After the addition of 30 g of sodium methoxide in 100 ml of methanol the mixture is refluxed for 15 hours, cooled, filtered and evaporated. The residue is dissolved in diethyl ether and filtered through a silica gel column to remove any unreacted 4-nitroaniline as its benzenesulfonate following addition of 17.4 g of benzenesulfonic acid. The filtrate is evaporated and the residue recrystallized from ethanol, to yield the 4-nitro-2-methylmercaptomethylaniline melting at 72°–77°.

The mixture of 9.3 g thereof, 8.6 g of 4-chlorophthalic anhydride and 200 ml of acetic acid is refluxed for 18 hours and evaporated. The residue is decolorized in diethyl ether with the aid of carbon, the mixture filtered and the filtrate concentrated to afford the N-(4-nitro-2-methylmercaptomethylphenyl)-4-chlorophthalimide melting at 112°–115°.

The solution of 1.8 g thereof in 10 ml of acetic acid is treated dropwise with 3 ml of 30% hydrogen peroxide while stirring at 70°–80°. After 3 hours the mixture is cooled, diluted with water, filtered and dried, to yield the N-(4-nitro-2-methylsulfonylmethylphenyl)-4-chlorophthalimide which does not melt under 250°.

The mixture of 1.5 g of N-(4-nitro-2-methylmercaptomethylphenyl)-4-chlorophthalimide and 50 ml of methyl iodide is refluxed for 6 days in the absence of light and evaporated. The residue is taken up in hot benzene, the mixture filtered and evaporated to yield the N-(4-nitro-2-iodomethylphenyl)-4-chlorophthalimide melting at 183°–187°.

The mixture of 1.0 g thereof, 12.4 g of freshly prepared silver carbonate, 58 ml of tetrahydrofuran and 10 ml of water is refluxed for 2 days in the absence of light, filtered and evaporated. The residue is taken up in ethyl acetate, the solution washed with water, dried and evaporated. The residue is chromatographed on silica gel and eluted with chloroform ethylacetate (9:1) to yield the N-(4-nitro-2-hydroxymethylphenyl)-4-chlorophthalimide.

EXAMPLE 4

The solution of 416 g of N-(4-nitro-o-tolyl)-4-chlorophthalimide in 28 lt. of hot ethyl acetate is cooled slightly and transferred under nitrogen to 250 ml (or 460 g) of a suspension of Raney nickel, which has been washed 4 times with anhydrous ethanol and 1 time with ethyl acetate, and 12 lt of ethyl acetate are used for the rinse. The mixture is hydrogenated at 3.4 atm. and 30° for approximately 8 hours, and continued for 2 hours after the hydrogen uptake has ceased. It is filtered, the residue rinsed with 15 lt. of ethyl acetate and the filtrate concentrated to about 14 lt. It is cooled, filtered, and the filtrate reduced to approximately 1 ½ lt to yield 2 crops of N-(4-amino-o-tolyl)-4-chlorophthalimide melting at 205°–207°; it is identical (but somewhat purer) than that obtained according to Example 2.

The starting material is prepared as follows: The mixture of 9.0 g of 4-chloro-o-xylene and the solution of 60.7 g of potassium permanganate in 280 ml of water is refluxed until the purple color disappears (about 7 hours) whereupon 3/4 of the water are distilled off and the remaining suspension is filtered while still hot. The residue is washed with hot water several times the clear and colorless filtrate (pH∼12) is concentrated to about 50 ml and acidified with 33 ml of concentrated hydrochloric acid. The cold mixture is extracted 3 times with ethyl acetate, the organic layer dried and evaporated to give the 4-chlorophthalic acid.

The solution of 7.76 g thereof in 75 ml of acetic anhydride is refluxed for 2 hours and evaporated. The residue is sublimed at 88°/0.35 mm Hg and recrystallized from diethyl ether yield the 4-chloro-phthalic anhydride melting at 93° to 94°.

To the solution of 276 g thereof in 4.2 lt. of glacial acetic acid 230 g of 4-nitro-o-toluidine are added while stirring and the mixture is heated for 45 minutes until dissolution occurs. It is refluxed for 4 hours, cooled, filtered and the residue washed with diethyl ether, to yield the N-(4-nitro-o-tolyl)-4-chlorophthalimide melting at 227°–229°.

EXAMPLE 5

The solution of 1.65 g of N-(2-ethyl-4-nitrophenyl)-4-chlorophthalimide in 80 ml of ethyl acetate is hydrogenated over 5 g of Raney Nickel at 2.5 atm. of hydrogen pressure for 5 hours. After filtration the residue of 1.5 g is crystallized from ethyl acetate-hexane to give 800 mg of the N-(2-ethyl-4-aminophenyl)-4-chlorophthalimide melting at 118°–120°.

The starting material is prepared as follows: The solution of 3.6 g of 4-chlorophthalic anhydride, 3.3 g of 2-ethyl-4-nitroaniline [L. Kirch et al, J. Org. Chem. 21, 1309 (1956)] and 55 ml of glacial acetic acid is refluxed for 4 hours. After cooling to room temperature, it is filtered and 4.6 g of crystalline N-(2-ethyl-4-nitrophenyl)-4-chlorophthalimide are collected, m.p. 147°–148°.

EXAMPLE 6

50 g (0.1744 mole) of N-(4-amino-o-tolyl-4-chlorophthalimide) are dissolved in 3.5 lt of acetone with mechanical stirring and slight warming until a clear solution is obtained. After cooling back to room temperature, the solution of 16.8 g of methane sulfonic acid in 200 ml of acetone is added all at once. Stirring is continued in an ice bath until the white precipitate reaches a fine granular from suitable for filtration. After filtration, the white, cakey residue is air dried first, then at 25°/0.5 mmHg, to give 61.0 g of N-(4-amino-o-tolyl)-4-chlorophthalimide methanesulfonate as a white powder melting at 275°.

EXAMPLE 7

The solution of 350 mg of N-(2-methoxymethyl-4-nitrophenyl)-4-chlorophthalimide is hydrogenated over 200 mg of 5% rhodium on carbon at 2.5 atmospheres of hydrogen pressure for 4 hours. After filtration from the catalyst, the residue is refluxed for 24 hours in 5 ml of xylene. After evaporation of the solvent, the residue is dissolved in acetone and the solution neutralized with ethereal hydrogen chloride, to yield the N-(2-methoxymethyl-4-aminophenyl)-4-chlorophthalimide hydrochloride melting at 255°–257°.

The starting material is prepared as follows: The solution of 2 g of N-(4-nitro-2-iodomethylphenyl)-4-chlorophthalimide in 40 ml of tetrahydrofuran and 40 ml of methanol, is treated with 8.7 g of freshly prepared silver carbonate for 20 hours, with protection from light. The mixture is filtered and the filtrate evaporated, to yield the N-(2-methoxymethyl-4-nitrophenyl)-4-chlorophthalimide melting at 125°–128°.

EXAMPLE 8

The solution of 300 mg of N-(2-ethoxymethyl-4-nitrophenyl)-4-chlorophthalimide in 40 ml of ethyl acetate is hydrogenated with 200 mg of 5% rhodium on carbon at 2.5 atmospheres of hydrogen pressure for 3 hours. After filtration from the catalyst the residue is refluxed for 24 hours in 5 ml of xylene, the solution evaporated and the residue crystallized from diethyl ether, to give the N-(2-ethoxymethyl-4-aminophenyl)-4-chlorophthalimide melting at 154°–156°.

The starting material is prepared as follows: The solution of 2 g of N-(4-nitro-2-iodomethylphenyl)-4-chlorophthalimide in 25 ml of tetrahydrofuran and 25 ml of ethanol, is stirred with 8.7 g of freshly prepared silver carbonate for 20 hours, with protection from light. The mixture is filtered and the filtrate evaporated, to yield the N-(2-ethoxymethyl-4-nitrophenyl)-4-chlorophthalimide.

EXAMPLE 9

The solution of 300 mg of N-(2-acetoxymethyl-4-nitrophenyl)-4-chlorophthalimide in 35 ml of ethyl acetate is hydrogenated with 200 mg of 5% rhodium on carbon at 2.5 atmospheres of hydrogen pressure for 3 hours. After filtration from the catalyst, the residue is crystallized from ethyl acetate-hexane to give the N-(2-acetoxymethyl-4-aminophenyl)-4-chlorophthalimide melting at 136°–138°.

The starting material is prepared as follows: The solution of 1.77 g of N-(4-nitro-2-iodomethylphenyl)-4-chlorophthalimide and 1.0 g of silver acetate in 32 ml of acetic acid is refluxed for one hour with protection from light. It is filtered, the filtrate evaporated and the residue recrystallized from ethyl acetate-diethyl ether, to yield the N-(2-acetoxymethyl-4-nitrophenyl)-4-chlorophthalimide melting at 124°–125°.

EXAMPLE 10

Preparation of 10,000 tablets each containing 100.0 mg of the active ingredient:

| Formula: | |
|---|---|
| N-(4-amino-o-tolyl)-4-chlorophthalimide | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

In the analogous manner tablets are prepared, containing any of the other compounds of the invention, preferably those illustrated by the preceding examples herein.

EXAMPLE 11

Preparation of 10,000 tablets each containing 100.0 mg of the active ingredient:

| Formula: | |
|---|---|
| N-(4-amino-o-tolyl)-4-chlorophthalimide | 50.00 g |
| Lactose | 72.25 g |

| Formula: | |
|---|---|
| Avicel PH 101 | 15.00 g |
| Corn starch | 12.00 g |
| Magnesium stearate | 0.75 g |
| Purified water | q.s. |

Procedure

All the powders are passed through a screen with openings of 0.6 mm. Then the drug substance, lactose, cellulose (Avicel) and 7.50 g of the corn starch are mixed in a suitable mixer. The remainder of the starch is suspended in 5 ml of water and the suspension added to 20 ml of boiling water. The paste formed is added to the powders which are granulated, if necessary, with an additional amount of water. The granulate is dried overnight at 40°, broken on a screen with 1.2 mm openings, blended with the magnesium stearate and compressed into tablets using concave punches with 10.3 mm diameter, uppers bisected.

In the analogous manner tablets are prepared, containing any of the other compounds of the invention, preferably those illustrated by the preceding examples herein.

We claim:

1. An N-(4-aminophenyl)-aromatic dicarboximide of the formula

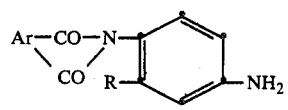

wherein Ar is chloro-1,2-phenylene and R is lower alkyl, (hydroxy, lower alkoxy or lower alkanoyloxy)-lower alkyl, or a pharmaceutically acceptable salt thereof.

2. A compound as claimed in claim 1, in which formula Ar is 4-chloro-1,2-phenylene and R is alkyl, α-(hydroxy, alkoxy or alkanoyloxy-alkyl) with up to 4 carbon atoms, or a therapeutically acceptable acid addition salt thereof.

3. A compound as claimed in claim 1, in which formula Ar is 4-chloro-1,2-phenylene and R is methyl, ethyl, or α-(hydroxy, methoxy, ethoxy or acetoxy)-(methyl or ethyl), or a therapeutically acceptable acid addition salt thereof.

4. A compound as claimed in claim 1 and being the N-(4-amino-o-tolyl)-4-chlorophthalimide, or a therapeutically acceptable acid addition salt thereof.

5. A compound as claimed in claim 4 and being the N-(4-amino-o-tolyl)-4-chlorophthalimide methanesulfonate.

* * * * *